(12) United States Patent
Bailey et al.

(10) Patent No.: US 7,125,881 B2
(45) Date of Patent: Oct. 24, 2006

(54) USE OF PYRIMIDINE—OR TRIAZINE—2 CARBONITILES FOR TREATING DISEASES ASSOCIATED WITH CYSTEINE PROSTEASE ACTIVITY AND NOVEL PYRIMIDINE-2-CARBONITILE DERIVATIVES

(75) Inventors: Andrew Bailey, Loughborough (GB); Garry Pairaudeau, Loughborough (GB); Anil Patel, Loughborough (GB); Stephen Thom, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/518,817

(22) PCT Filed: Jun. 23, 2003

(86) PCT No.: PCT/SE03/01078

§ 371 (c)(1),
(2), (4) Date: Dec. 20, 2004

(87) PCT Pub. No.: WO04/000819

PCT Pub. Date: Dec. 31, 2003

(65) Prior Publication Data

US 2005/0222152 A1    Oct. 6, 2005

(30) Foreign Application Priority Data

Jun. 24, 2002    (SE) .................................. 0201976

(51) Int. Cl.
*A61K 31/505* (2006.01)
*A61K 31/506* (2006.01)
*A61P 19/02* (2006.01)
*C07D 239/42* (2006.01)

(52) U.S. Cl. ...................... 514/269; 514/256; 544/298; 544/319; 544/326

(58) Field of Classification Search ................ 544/319, 544/298; 514/269, 256
See application file for complete search history.

(56) References Cited

U.S. PATENT DOCUMENTS 5,759,956 A * 6/1998 Niedermann et al. ....... 504/235

2004/0249153 A1 * 12/2004 Altmann et al. ............ 544/319

FOREIGN PATENT DOCUMENTS

| DE | 870304 | * | 3/1953 |
| JP | 06135942 | * | 5/1994 |
| WO | WO 9709315 A1 | | 3/1997 |
| WO | WO 0055125 | | 9/2000 |
| WO | WO 0232879 A1 | | 4/2002 |
| WO | WO 03020278 A1 | | 3/2003 |

OTHER PUBLICATIONS

West, Anthony R., Solid State Chemistry and its Applications, Wiley, New York, 1988, pp. 358 & 365.*
Vippagunta et al., Advanced Drug Delivery Reviews 48: 3-26, 2001.*
Hou et al. Arthritis & Rheumatism, 46(3): 663-674, 2002.*
Tomota JP 06135942, CA 121: 179610, 1994.*
International Search Report.

* cited by examiner

*Primary Examiner*—Venkataraman Balasubramanian
(74) *Attorney, Agent, or Firm*—Jianzhong Shen

(57) ABSTRACT

The present invention therefore provides use of a compound of formula (I) and compositions for treating diseases associated with cysteine protease activity. The compounds are reversible inhibitors of cysteine proteases S, K, F, L and B. Of particular interest are diseases associated with Cathepsin S. In addition, this invention also discloses processes for the preparation of such inhibitors

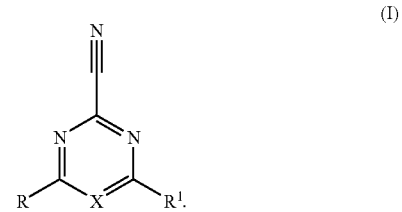

7 Claims, No Drawings

USE OF PYRIMIDINE—OR TRIAZINE—2 CARBONITILES FOR TREATING DISEASES ASSOCIATED WITH CYSTEINE PROSTEASE ACTIVITY AND NOVEL PYRIMIDINE-2-CARBONITILE DERIVATIVES

CROSS-REFERENCE TO RELATED APPLICATIONS

This application is a US National Stage under 35 U.S.C § 371 of International Application No. PCT/SE2003/001078 that was filed on Jun. 23, 2003. The International Application claims priority under 35 U.S.C § 119(a)–(d) to Swedish Application No. 0201976-8 filed Jun. 24, 2002.

The present invention relates to compounds and compositions for treating diseases associated with cysteine protease activity. The compounds are reversible inhibitors of cysteine proteases S, K, F, L and B. Of particular interest are diseases associated with Cathepsin S. In addition this invention also discloses processes for the preparation of such inhibitors.

BACKGROUND OF THE INVENTION

Cathepsin S is a member of the papain superfamily of cysteine proteases which also encompasses Cathepsins B, H, L, O and K. Cathepsin S plays a key role in the processing of invariant chain in MHC class II complexes allowing the complex to associate with antigenic peptides. MHC class II complexes are then transported to the surface of the cell for presentation to effector cells such as T cells. The process of antigen presentation is a fundamental step in initiation of the immune response. In this respect inhibitors of cathepsin S could be useful agents in the treatment of inflammation and immune disorders such as, but not limited to, asthma, rheumatoid arthritis, multiple sclerosis and Crohn's disease. Cathepsin S has also been implicated in a variety of other diseases involving extracellular proteolysis such as the development of emphysema in COPD through degradation of elastin and in Alzheimers disease.

Other Cathepsins notably K and L have been shown to degrade bone collagen and other bone matrix proteins. Inhibitors of these cysteine proteases would be expected to be useful in the treatment of diseases involving bone resorption such as osteoporosis.

The present invention therefore provides use of a compound of formula (I)

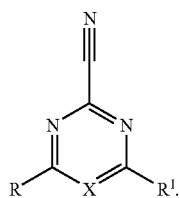

(I)

in which:

X is N or CA where A is hydrogen, halogen, $CHR^2R^3$, $OR^2$, $NR^2R^3$, $SR^2$;

$R^2$ and $R^3$ are independently hydrogen, $C_{1-6}$ alkyl or $C_{3-6}$ cycloalkyl both of which can optionally contain one or more O, S or $NR^4$ groups where $R^4$ is hydrogen or $C_{1-6}$ alkyl, and can be optionally substituted by aryl, heteroaryl, $NR^5R^6$ where $R^5$ and $R^6$ together with the nitrogen atom to which they are attached form a 4–7 membered ring optionally containing a further O, S, $NR^4$, or R2 and R3 together with the nitrogen atom to which they are attached form a 4–7 membered ring optionally containing a further O, S, $NR^4$ group, or R2 and R3 are aryl or heteroaryl groups, both aryl and heteroaryl groups being optionally substituted by halogen, amino, hydroxy, cyano, nitro, carboxy, $CONR^7R^8$, $SO_2NR^7R^8$, $SO_2R^4$, trifluoromethyl, $NHSO_2R^4$, $NHCOR^4$, ethylenedioxy, methylenedioxy, $C_{1-6}$ alkyl, $C_{1-6}$ alkoxy, $NR^7R^8$ or $SR^7$ where $R^7$ and $R^8$ are independently hydrogen or $C_{1-6}$ alkyl;

R and $R^1$ are independently a group $Y(CH_2)pR^9$ where p is 0, 1, 2 or 3 and Y is O or $NR^{10}$ where $R^{10}$ is hydrogen, $C_{1-6}$ alkyl or $C_{3-6}$ cycloalkyl;

and $R^9$ is hydrogen, $C_{1-6}$ alkyl which can optionally contain one or more O, S or $NR^4$ groups where $R^4$ is hydrogen or $C_{1-6}$ alkyl, or a 3 to 7-membered saturated ring optionally containing a carbonyl group, one or more O, S or N atoms, or an aryl or heteroaryl group containing one to four heteroatoms selected from O, S or N, the saturated ring, aryl and heteroaryl groups all being optionally substituted by halogen, amino, hydroxy, cyano, nitro, carboxy, $CONR^7R^8$, $SO_2NR^7R^8$, $SO_2R^4$, trifluoromethyl, $NHSO_2R^4$, $NHCOR^4$, ethylenedioxy, methylenedioxy, $C_{1-6}$ alkyl, $C_{1-6}$ alkoxy, $SR^5$ or $NR^{11}R^{12}$ where $R^{11}$ and $R^{12}$ are independently hydrogen, $C_{1-6}$ alkyl or together with the nitrogen atom to which they are attached form a 5- or 6-membered saturated ring optionally containing a further O, S or $NR^4$ group;

or R/$R^1$ is a group $NR^{10}(CHR^{10})CONR^2R^3$ or $NR^{10}(CH_2)_q CONR^2R^3$ where q is 1, 2 or 3;

or R/$R^1$ is a group $NR^{13}R^{14}$ where $R^{13}$ and $R^{14}$ together with the nitrogen atom to which they are attached form a 4 to 7-membered saturated ring optionally containing a carbonyl group, O, S or N atom and optionally substituted by $C_{1-6}$ alkyl, amino, hydroxy, $CO_2C_{1-6}$ alkyl, halogen, $NR^5R^6$, $NR^7R^8$, $C_{1-6}$ alkyl$NR^{17}R^{18}$ where $R^{17}$ and $R^{18}$ are independently hydrogen or $C_{1-6}$ alkyl, $CONR^{15}R^{16}$ where $R^{15}$ and $R^{16}$ are independently hydrogen or $C_{1-6}$ alkyl, or optionally substituted by aryl, phenoxy, COphenyl, or a heteroaryl group, the latter four groups being optionally substituted by halogen, amino, hydroxy, cyano, nitro, carboxy, $CONR^7R^8$, $SO_2NR^7R^8$, $SO_2R^4$, trifluoromethyl, $NHSO_2R^4$, $NHCOR^4$, ethylenedioxy, methylenedioxy, $C_{1-6}$ alkyl, $C_{1-6}$ alkoxy, $SR^5$ or $NR^{11}R^{12}$ where $R^{11}$ and $R^{12}$ are independently hydrogen, $C_{1-6}$ alkyl or together with the nitrogen atom to which they are attached form a 5- or 6-membered saturated ring optionally containing a further O, S or $NR^4$ group;

and pharmaceutically acceptable salts or solvates thereof, in the manufacture of a medicament for use in the inhibition of cathepsin S in a mammal such as man.

In the context of the present specification, unless otherwise indicated, an alkyl or alkenyl group or an alkyl or alkenyl moiety in a substituent group may be linear or branched. Aryl groups include phenyl and naphthyl. Heteroaryl groups include 5- or 6-membered, 5,6- or 6,6-fused heterocyclic rings containing one or more heteroatoms selected from N, S, O. Examples include pyridine, pyrimidine, thiazole, oxazole, pyrazole, imidazole, furan, thiophene, quinoline, isoquinoline, benzimidazole, benzofuran, benzothiophene and indole.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

Preferably X is CH, $NHR^2$, $OR^2$ where $R^2$ is preferably H or $C_{1-6}$ alkyl.

Preferably R is a group $Y(CH_2)_p R^7$ where p is 0 or 1 and Y is $NR^8$ where $R^8$ is hydrogen and $R^7$ is substituted phenyl. Preferably $R^7$ is phenyl substituted by halogen, especially chloro. More preferably $R^7$ is phenyl substituted by chloro in the 4-position.

Preferably $R^1$ is a group $NR^{13}R^{14}$ where $R^{13}$ and $R^{14}$ together with the nitrogen atom to which they are attached form a morpholine ring, piperidine or piperazine ring optionally substituted, or $R^1$ is a group $NR^9R^{10}$ where $R^{10}$ is H or $C_{1-6}$ alkyl and $R^9$ is $C_{1-6}$ alkyl which can optionally contain one or more O, S or $NR^4$ groups where $R^4$ is hydrogen or $C_{1-6}$ alkyl.

The most preferred substituents for R and $R^1$ are those of the examples exemplified herein.

Preferred compounds of the invention include:
4-[(4-Chlorophenyl)amino]-6-(dimethylamino)-1,3,5-triazine-2-carbonitrile,
4-Morpholin-4-yl-6-(4-phenoxypiperidin-1-yl)-1,3,5-triazine-2-carbonitrile,
4-[(4-Chlorophenyl)amino]-6-morpholin-4-yl-1,3,5-triazine-2-carbonitrile,
4-(7-Azabicyclo[2.2.1]hept-7-yl)-6-[(4-chlorophenyl) amino]-1,3,5-triazine-2-carbonitrile,
4-[(4-Chlorophenyl)amino]-6-pyrrolidin-1-yl-1,3,5-triazine-2-carbonitrile,
4-[(4-Chlorophenyl)amino]-6-piperidin-1-yl-1,3,5-triazine-2-carbonitrile,
4-[(4-Chlorophenyl)amino]-6-(ethylamino)-1,3,5-triazine-2-carbonitrile,
4-[(4-Chlorophenyl)amino]-6-(3-hydroxypyrrolidin-1-yl)-1,3,5-triazine-2-carbonitrile,
4-[(4-Chlorophenyl)amino]-6-[(2-piperidin-1-ylethyl) amino]-1,3,5-triazine-2-carbonitrile,
4-[(4-Chlorophenyl)amino]-6-(4-phenylpiperidin-1-yl)-1,3, 5-triazine-2-carbonitrile,
4-[(3-Chlorobenzyl)amino]-6-(dimethylamino)-1,3,5-triazine-2-carbonitrile,
4-Morpholin-4-yl-6-[(4-morpholin-4-ylphenyl)amino]-1,3, 5-triazine-2-carbonitrile,
4-(2,3-Dihydro-1,4-benzodioxin-6-ylamino)-6-morpholin-4-yl-1,3,5-triazine-2-carbonitrile,
4-Morpholin-4-yl-6-(3-phenylpiperidin-1-yl)-1,3,5-triazine-2-carbonitrile,
4-(1,4'-Bipiperidin-1'-yl)-6-morpholin-4-yl-1,3,5-triazine-2-carbonitrile,
4-[4-(1H-Imidazol-1-yl)piperidin-1-yl]-6-morpholin-4-yl-1, 3,5-triazine-2-carbonitrile,
4-[4-(4-Chlorobenzoyl)piperidin-1-yl]-6-morpholin-4-yl-1, 3,5-triazine-2-carbonitrile,
4-[4-(5-Chloropyridin-2-yl)piperazin-1-yl]-6-morpholinyl-1,3,5-triazine-2-carbonitrile,
4-Morpholin-4-yl-6-{[3-(2-oxopyrrolidin-1-yl)propyl] amino}-1,3,5-triazine-2-carbonitrile,
1-(4-Cyano-6-morpholin-4-yl-1,3,5-triazin-2-yl)-N,N-diethylpiperidine-3-carboxamide,
4-[4-(2-Methoxyphenyl)piperazin-1-yl]-6-morpholin-4-yl-1,3,5-triazine-2-carbonitrile,
N~2~-(4-Cyano-6-morpholin-4-yl-1,3,5-triazin-2-yl)-N~1~,N~1~-bis{4-[N-(4-cyano-6-morpholin-4-yl-1,3,5-triazin-2-yl)-N-isobutylglycyl]morpholin-3-yl}-N~2~-isobutylglycinamide,
4-Morpholin-4-yl-6-[(2-pyridin-3-ylethyl)amino]-1,3,5-triazine-2-carbonitrile,
4-{[2-(2-Furyl)ethyl]amino}-6-morpholin-4-yl-1,3,5-triazine-2-carbonitrile,
4[(4-Chlorophenyl)amino]-6-(4-methylpiperazin-1-yl)-1,3, 5-triazine-2-carbonitrile,
4-Azetidin-1-yl-6-[(4-chlorophenyl)amino]-1,3,5-triazine-2-carbonitrile,
4-[(4-Chlorophenyl)amino]-6-morpholin-4-ylpyrimidine-2-carbonitrile,
4-[(4-Methylcyclohexyl)amino]-6-morpholin-4-ylpyrimidine-2-carbonitrile,
4-(4-Chlorophenoxy)-6-morpholin-4-ylpyrimidine-2-carbonitrile,
4-[(4-Chlorophenyl)amino]-6-(dimethylamino)pyrimidine-2-carbonitrile,
4-[(1-Methylpiperidin-4-yl)amino]-6-morpholin-4-ylpyrimidine-2-carbonitrile,
4-(Cyclohexylamino)-6-morpholin-4-ylpyrimidine-2-carbonitrile,
4-[(4-Chlorophenyl)amino]-6-pyrrolidin-1-ylpyrimidine-2-carbonitrile,
4-[(6-Chloropyridin-3-yl)amino]-6-morpholin-4-ylpyrimidine-2-carbonitrile,
1-{6-[(4-Chlorophenyl)amino]-2-cyanopyrimidin-4-yl}-L-prolinamide,
4-(4-Aminopiperidin-1-yl)-6-[(4-chlorophenyl)amino]pyrimidine-2-carbonitrile,
4-[(4-Chlorophenyl)amino]-6-(4-pyrrolidin-1-ylpiperidin-1-yl)pyrimidine-2-carbonitrile,
4-[(4-Chlorophenyl)amino]-6-[(3-pyrrolidin-1-ylpropyl) amino]pyrimidine-2-carbonitrile,
tert-Butyl 4-{6-[(4-chlorophenyl)amino]-2-cyanopyrimidin-4-yl}piperazine-1-carboxylate,
4-[(4-Chlorophenyl)amino]-6-(cyclopropylamino)pyrimidine-2-carbonitrile,
4-[(4-Chlorophenyl)amino]-6-piperazin-1-ylpyrimidine-2-carbonitrile,
(2S)-N~2~-{6-[(4-Chlorophenyl)amino]-2-cyanopyrimidin-4-yl}-N~1~,N~1~-bis[4-(N-{6-[(4-chlorophenyl) amino]-2-cyanopyrimidin-4-yl}-L-leucyl)morpholin-3-yl]-L-leucinamide,
5-Chloro-4-[(4-chlorophenyl)amino]-6-morpholin-4-ylpyrimidine-2-carbonitrile,
4-[(4-Chlorophenyl)amino]-5-methoxy-6-piperazin-1-ylpyrimidine-2-carbonitrile,
4-[(4-Chlorophenyl)amino]-5-methoxy-6-morpholin-4-ylpyrimidine-2-carbonitrile,
4-[(3S)-3-Aminopyrrolidin-1-yl]-6-[(4-chlorophenyl) amino]-5-methoxypyrimidine-2-carbonitrile,
4-[(4-Chlorophenyl)amino]-6-{4-[3-(dimethylamino)propyl]piperazin-1-yl}-5-methoxypyrimidine-2-carbonitrile,
4-[(4-Chlorophenyl)amino]-6-(dimethylamino)-5-methoxypyrimidine-2-carbonitrile,
4-[(4-Chlorophenyl)amino]-5-methoxy-6-(3-oxopiperazin-1-yl)pyrimidine-2-carbonitrile,
1-{6-[(4-Chlorophenyl)amino]-2-cyano-5-methoxypyrimidin-4-yl}piperidine-3-carboxamide,
4-(4-Aminopiperidin-1-yl)-6-[(4-chlorophenyl)amino]-5-methoxypyrimidine-2-carbonitrile,
5-Amino-4-[(4-chlorophenyl)amino]-6-morpholin-4-ylpyrimidine-2-carbonitrile,
5-Amino-4[(4-Chlorophenyl)amino]-6-(ethylamino)pyrimidine-2-carbonitrile, and pharmaceutically acceptable salts thereof.

In a further aspect the invention provides a compound of formula (I) as defined above but where X is CH, NHR², OR² where R² is preferably H or C$_{1-6}$ alkyl. For the novel compounds of the invention other preferred groups and compounds are those defined above.

The present invention further provides a process for the preparation of a compound of formula (I) which comprises (i) reaction of a compound of general formula (II)

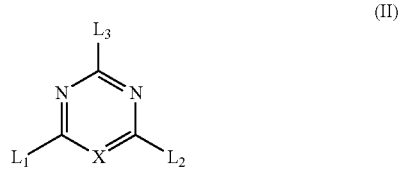

(II)

wherein L1, L2 and L3 represent a leaving group (e.g. halide, sulphide, sulfoxide or sulphone group), preferably the sulphide is oxidised to a sulphoxide or sulphone group before displacement. An oxidising agent such as a peracid may be used, for example meta-chloroperbenzoic acid in dichloromethane at room temperature.

L1 and L2 may be displaced by R and R¹ respectively where R and R¹ are defined in formula (I) and L3 may be displaced by a cyanide salt. The sequence of displacement of L1, L2 and L3 may be varied.

When X=CA and A=OR², SR² or CHR²R³ compounds of general formula (ID) may be formed by treatment of compounds of general formula (III) and (IV) with phosphorous oxychloride at reflux. R¹⁹ is preferably C$_{1-6}$ alkyl or benzyl

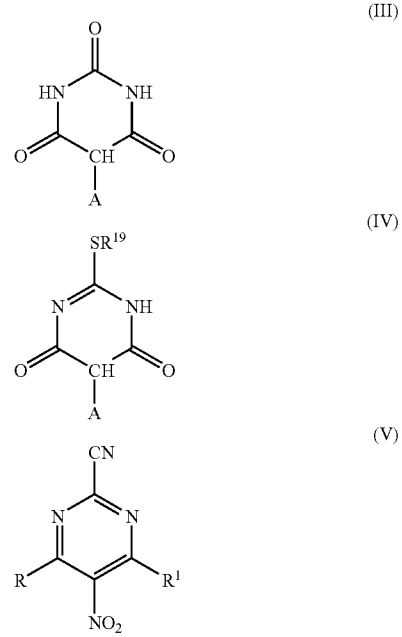

(ii) when X=CA and A=NH₂ reaction of a compound of general formula (V) under a hydrogen atmosphere with palladium catalyst at room temperature.

According to a further feature of the invention there is provided a compound of the formula (I), or a pharmaceutically acceptable salt thereof, for use as a therapeutic agent.

According to a further feature of the present invention there is provided a method for producing inhibition of a cysteine protease in a warm blooded animal, such as man, in need of such treatment, which comprises administering to said animal an effective amount of a compound of the present invention, or a pharmaceutically acceptable salt thereof The invention also provides a compound of the formula (I), or a pharmaceutically acceptable salt thereof, for use as a medicament; and the use of a compound of the formula (I) of the present invention, or a pharmaceutically acceptable salt thereof, in the manufacture of a medicament for use in the inhibition of a cysteine protease in a warm blooded animal, such as man. In particular the compounds of the invention are useful in the treatment of inflammation and immune disorders such as asthma, rheumatoid arthritis, COPD, multiple sclerosis, Crohn's disease, Alzheimers and pain, such as neuropathic pain. Preferably the compounds of the invention are used to treat pain, in particular neuropathic pain.

In particular the invention provides the use of a compound of the formula (I) of the present invention, or a pharmaceutically acceptable salt thereof, in the manufacture of a medicament for use in the inhibition of Cathepsin S in a warm blooded animal, such as man. In order to use a compound of the formula (I) or a pharmaceutically acceptable salt thereof for the therapeutic treatment of mammals including humans, in particular the inhibition of a cysteine protease, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt thereof and a pharmaceutically acceptable diluent or carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule which contains between 100 mg and 1 g of the compound of this invention.

In another aspect a pharmaceutical composition of the invention is one suitable for intravenous, subcutaneous or intramuscular injection.

Each patient may receive, for example, an intravenous, subcutaneous or intramuscular dose of 1 mgkg⁻¹ to 100 mgkg⁻¹ of the compound, preferably in the range of 5 mgkg⁻¹ to 20 mgkg⁻¹ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The following illustrate representative pharmaceutical dosage forms containing the compound of formula (I), or a pharmaceutically-acceptable salt thereof (hereafter compound X), for therapeutic or prophylactic use in humans:

(a)

| Tablet I | mg/tablet |
|---|---|
| Compound X. | 100 |
| Lactose Ph.Eur. | 179 |
| Croscarmellose sodium | 12.0 |
| Polyvinylpyrrolidone | 6 |
| Magnesium stearate | 3.0 |

(b)

| Tablet II | mg/tablet |
|---|---|
| Compound X | 50 |
| Lactose Ph.Eur. | 229 |
| Croscarmellose sodium | 12.0 |
| Polyvinylpyrrolidone | 6 |
| Magnesium stearate | 3.0 |

(c)

| Tablet III | mg/tablet |
|---|---|
| Compound X | 1.0 |
| Lactose Ph.Eur. | 92 |
| Croscarmellose sodium | 4.0 |
| Polyvinylpyrrolidone | 2.0 |
| Magnesium stearate | 1.0 |

(d)

| Capsule | mg/capsule |
|---|---|
| Compound X | 10 |
| Lactose Ph.Eur. | 389 |
| Croscarmellose sodium | 100 |
| Magnesium stearate | 1. |

(e)

| Injection I | (50 mg/ml) |
|---|---|
| Compound X | 5.0% w/v |
| Isotonic aqueous solution | to 100% |

Buffers, pharmaceutically-acceptable cosolvents such as polyethylene glycol, polypropylene glycol, glycerol or ethanol or complexing agents such as hydroxy-propyl β cyclodextrin may be used to aid formulation.

Note

The above formulations may be obtained by conventional procedures well known in the pharmaceutical art. The tablets (a)–(c) may be enteric coated by conventional means, for example to provide a coating of cellulose acetate phthalate.

The following examples illustrate the invention.

EXAMPLE 1

4-[(4-Chlorophenyl)amino]-6-(dimethylamino)-1,3,5-triazine-2-carbonitrile (i) 4,6-Dichloro-N-4-chlorophenyl)-1,3,5-triazin-2-amine 4-Chloroaniline (8.28 g) was added to a mixture of trichlorotriazine (6 g) in acetone/ice-water (1:1, 60 ml) and stirred for 1 h. The solid was filtered and dried to give a light brown solid, 8.5 g.

MS: APCI(+ve) 275/7(M+1)

(ii) 6-Chloro-N~2~-(4-chlorophenyl)-N~4~,N~4~-dimethyl-1,3,5-triazine-2,4-diamine A solution of dimethylamine in tetrahydrofuran (2M, 1.1 ml) was added to a mixture of the product from step (i) (0.3 g) in acetone (10 ml) and ice-water (10 ml). After stirring for 1 h, the solid was filtered, washed with water and dried. Yield 0.3 g solid.

MS: APCI(+ve) 284(M+1)

(iii) 4-[(4-Chlorophenyl)amino]-6-dimethylamino)-1,3,5-triazine-2-carbonitrile

Sodium cyanide (0.138 g) was added to a solution of the product from step (ii) (0.4 g) in N,N-dimethylformamide (20 ml) and heated at 90° C. for 16 h. The mixture was partitioned between ethyl acetate and water, a solid formed which was filtered off and purified by RPHPLC 15–85% acetonitrile in aqueous trifluoroacetic acid. Yield 0.05 g MS: APCI(+ve) 275(M+1) 1H NMR: (DMSO-d6) δ 10.30(1H, bs), 7.72–7.37(4H, 2×d), 3.14(6H, s)

EXAMPLE 2

4-Morpholin-4-yl-6-(4-phenoxypiperidin-1-yl)-1,3,5-triazine-2-carbonitrile (i) 2,4-Dichloro-6-morpholin-4-yl-1,3,5-triazine Morpholine was added dropwise to stirred solution of trichlorotriazine (6.7 g), N,N-diisopropylethylamine (60.5 ml) in dichloromethane (50 ml) at −78° C. The solid formed was filtered off, washed with water, dried to give a white solid (6.7 g).

MS: APCI(+ve) 235(M+1)

(ii) 4-Morpholin-4-yl-6-(4-phenoxypiperidin-1-yl)-1,3,5-triazine-2-carbonitrie

4-Phenoxypiperidine (0.15 g) was added to a solution of the product from step (i) (0.2 g), N,N-diisopropylethylamine (1.47 ml) in tetrahydrofuran and stirred at room temperature for 16 h. The solvent was evaporated under reduced pressure and the residue purified by chromatography on silica eluting with ether/isohexane (1:2). Yield 0.3 g white solid. The solid was dissolved in N,N-dimethylformamide (20 ml), sodium cyanide (0.1 g) added and heated at 90° C. for 32 h. The mixture was partitioned between ethyl acetate and water, the organic layer separated, washed with water, brine, dried (MgSO4) and evaporated under reduced pressure. The residue was purified by RPHPLC 35–95% acetonitrile in aqueous trifluoroacetic acid. Yield 0.079 g MS: APCI(+ve) 367(+H) 1H NMR: (DMSO-d6) δ 7.31–6.91(5H, m), 4.66(1H, m), 4.11–4.04(2H, m), 3.70–3.57(10H, m), 2.00–1.95(2H, m), 1.63–1.60(2H, m)

EXAMPLES 3–26

Examples 3–26 were prepared according to the methods of example 1 or 2 using the appropriate amines.

EXAMPLE 3

4-[(4-Chlorophenyl)amino]-6-morpholin-4-yl-1,3,5-triazine-2-carbonitrile

MS: APCI(−ve) 315(M−1) 1H NMR: (DMSO-d6) δ 10.41(1H, bs), 7.66–7.31(4H, 2×d), 3.74–3.64(8H, m)

EXAMPLE 4

4-(7-Azabicyclo[2.2.1]hept-7-yl)-6-[(4-chlorophenyl)amino]-1,3,5-triazine-2-carbonitrile MS: APCI(−ve) 325(M−1) 1H NMR: (DMSO-d6) δ 10.37(1H, bs), 7.70–7.35(4H, 2×d), 4.64–4.61(2H, m), 1.74–1.52(8H, m)

EXAMPLE 5

4-[(4-Chlorophenyl)amino]-6-pyrrolidin-1-yl-1,3,5-triazine-2-carbonitrile

MS: APCI(−ve) 299(M−1) 1H NMR: (DMSO-d6) δ 10.29(1H, bs), 7.75–7.36(4H, 2×d), 3.54–3.49(4H, m), 1.96–1.90(4H, m)

EXAMPLE 6

4-[(4-Chlorophenyl)amino]-6-piperidin-1-yl-1,3,5-triazine-2-carbonitrile

MS: APCI(−ve) 313(M−1) 1H NMR: (DMSO-d6) δ 10.29(1H, bs), 7.66–7.38(4H, 2×d), 3.74–3.73(4H, m), 1.64–1.55(6H, m)

EXAMPLE 7

4-[(4-Chlorophenyl)amino]-6-(ethylamino)-1,3,5-triazine-2-carbonitrile

MS: APCI(−ve) 273(M−1) 1H NMR: (DMSO-d6) δ 10.31(1H, bs), 8.39–7.34(5H, m), 3.36–3.27(2H, q), 1.10 (3H, t)

EXAMPLE 8

4-[(4-Chlorophenyl)amino]-6-(3-hydroxypyrrolidin-1-yl)-1,3,5-triazine-2-carbonitrile MS: APCI(−ve) 315(M−1) 1H NMR: (DMSO-d6) δ 10.31(1H, s), 7.76–7.38 (4H, m), 5.06(1H, m), 4.38(1H, m), 366–3.45(4H, m), 2.04–1.95(2H, m)

EXAMPLE 9

4-[(4-Chlorophenyl)amino]-6-[(2-piperidin-1-yl-ethyl)amino]-1,3,5-triazine-2-carbonitrile MS: APCI(+ve) 358(M+1) 1H NMR: (DMSO-d6) δ 10.38(1H, s), 8.35–7.34(5H, m), 3.37(2H, m), 2.43–2.34 (6H, m), 1.48–1.44(6H, m)

EXAMPLE 10

4-[(4-Chlorophenyl)amino]-6-(4-phenylpiperidin-1-yl)-1,3,5-triazine-2-carbonitrile MS: APCI(−ve) 389(M−1) 1H NMR: (DMSO-d6) δ 10.33(1H, bs), 7.68–7.16(9H, m), 4.72–4.69(2H, d), 3.09–2.85(3H, m), 1.88–1.55(4H, m)

EXAMPLE 11

4-[(3-Chlorobenzyl)amino]-6-(dimethylamino)-1,3,5-triazine-2-carbonitrile

MS: APCI(−ve) 287(M−1) 1H NMR: (DMSO-d6) δ 8.59–8.44(1H, t), 7.37–7.22(4H, m), 4.47–4.44(2H, m), 3.07–3.03(6H, m)

EXAMPLE 12

4-Morpholin-4-yl-6-[(4-morpholin-4-ylphenyl)amino]-1,3,5-triazine-2-carbonitrile MS: APCI(+ve) 368(M+1) 1H NMR: (DMSO-d6) δ 10.09(1H, s), 7.57–7.48(2H, d), 6.93–6.84(2H, d), 3.72–3.55 (12H, m), 3.07–3.00(4H, m)

EXAMPLE 13

4-(2,3-Dihydro-1,4-benzodioxin-6-ylamino)-6-morpholin-4-yl-1,3,5-triazine-2-carbonitrile MS: APCI(−ve) 339(M−1) 1H NMR: (DMSO-d6) δ 10.13(1H, s), 7.21–6.80(3H, m), 4.23–3.64(12H, m)

EXAMPLE 14

4-Morpholin-4-yl-6-(3-phenylpiperidin-1-yl)-1,3,5-triazine-2-carbonitrile

MS: APCI(+ve) 351(M+1) 1H NMR: (DMSO-d6) δ 7.35–7.22(5H, m), 4.67–2.64(13H, m), 1.93–1.48(4H, m)

EXAMPLE 15

4-(1,4'-Bipiperidin-1'-yl)-6-morpholin-4-yl-1,3,5-triazine-2-carbonitrile, trifluoroacetate salt MS: APCI(+ve) 358(M+1) 1H NMR: (DMSO-d6) δ 9.23 (1H, bm), 4.75–4.64(2H, m), 3.71–3.36(11H, m), 2.93–2.87 (4H, m), 2.08–1.37(10H, m)

EXAMPLE 16

4-[4-(1H-Imidazol-1-yl)piperidin-1-yl]-6-morpholin-4-yl-1,3,5-triazine-2-carbonitrile MS: APCI(+ve) 341(M+1) 1H NMR: (DMSO-d6) δ 9.11 (11H, s), 7.89–7.88(1H, s), 7.69–7.68(1H, s), 4.79–4.62(3H, m), 3.74–3.02(10H, m), 2.17–1.88(4H, m)

EXAMPLE 17

4-[4-(4-Chlorobenzoyl)piperidin-1-yl]-6-morpholin-4-yl-1,3,5-triazine-2-carbonitrile MS: APCI(+ve) 413(M+1) 1H NMR: (DMSO-d6) δ 8.04–8.02(2H, d), 7.64–7.60(2H, d), 4.62–4.52(2H, m), 3.80–3.69(5H, m), 3.32–3.08(61H, m), 1.87–1.43(4H, m)

EXAMPLE 18

4-[4-(5-Chloropyridin-2-yl)piperazin-1-yl]-6-morpholin-4-yl-1,3,5-triazine-2-carbonitrile MS: APCI(+ve) 387(M+1) 1H NMR: (DMSO-d6) δ 8.14–8.13(1H, s), 7.65–7.62(1H, d), 6.91–6.89(1H, d), 3.82–3.57(16H, m)

EXAMPLE 19

4-Morpholin-4-yl-6-{[3-(2-oxopyrrolidin-1-yl)propyl]amino}-1,3,5-triazine-2-carbonitrile MS: APCI(+ve) 332(M+1) 1H NMR: (DMSO-d6) δ 8.10–8.07(1H, t), 3.70–3.62(8H, m), 3.39–3.17(6H, m), 2.22–1.62(6H, m)

EXAMPLE 20

1-(4-Cyano-6-morpholin-4-yl-1,3,5-triazin-2-yl)-N,N-diethylpiperidine-3-carboxamide MS: APCI(+ve) 374(M+1) 1H NMR: (DMSO-d6) δ 4.39 (2H, m), 3.78–3.60(4H, m), 3.33–2.63(11H, m), 1.80–1.43 (4H, m), 1.16–0.92(6H, m)

EXAMPLE 21

4-[4-(2-Methoxyphenyl)piperazin-1-yl]-6-morpholin-4-yl-1,3,5-triazine-2-carbonitrile MS: APCI(+ve) 382(M+1) 1H NMR: (DMSO-d6) δ 6.99–6.87(4H, m), 3.86–3.63(15H, m), 2.99(4H, m)

EXAMPLE 22

N~2~-(4-Cyano-6-morpholin-4-yl-1,3,5-triazin-2-yl)-N~1~,N~1~-bis{4-[N-4-cyano-6-morpholin-4-yl-1,3,5-triazin-2-yl)-N-isobutylglycyl]morpholin-3-yl}-N~2~-isobutylglycinamide MS: APCI(+ve) 390(M+1) 1H NMR: (DMSO-d6) δ 4.39–4.36(2H, d), 3.62–3.31(18H, m), 2.05–1.92(1H, m), 0.87–0.85(6H, d)

EXAMPLE 23

4-Morpholin-4-yl-6-[(2-pyridin-3-ylethyl)amino]-1,3,5-triazine-2-carbonitrile, trifluoroacetate salt MS: APCI(+ve) 312(M+1) 1H NMR: (DMSO-d6) δ 8.69–8.64(2H, m), 8.22–8.04(2H, m), 7.78–7.70(1H, m), 3.66–3.53(10H, m), 2.97–2.93(2H, t)

EXAMPLE 24

4-{[2-(2-Furyl)ethyl]amino}-6-morpholin yl-1,3,5-triazine-2-carbonitrile

MS: APCI(–ve) 299(M+1) 1H NMR: (DMSO-d6) δ 8.21 (1H, t), 7.51(1H, s), 6.34(1H, s), 6.15(1H, s), 3.64–3.62(8H, m), 3.52–3.46(2H, m), 2.86–2.82(2H, m)

EXAMPLE 25

4-[(4-Chlorophenyl)amino]-6-(4-methylpiperazin-1-yl)-1,3,5-triazine-2-carbonitrile, trifluoroacetate salt MS: APCI(+ve) 330(M+1) 1H NMR: (DMSO-d6) δ 10.56(1H, bs), 10.05(1H, brs), 7.66–7.40(4H, m), 3.41–3.35 (8H, m), 2.81(3H, s)

EXAMPLE 26

4-Azetidin-1-yl-6-[(4-chlorophenyl)amino]-1,3,5-triazine-2-carbonitrile

MS: APCI(–ve) 285(M–1) 1H NMR: (DMSO-d6) δ 10.32(1H, s), 7.72–7.32(4H, m), 4.15–4.10(4H, m), 2.38–2.30(2H, q)

EXAMPLE 27

4-[(4-Chlorophenyl)amino]-6-morpholin-4-ylpyrimidine-2-carbonitrile (i) N-(4-Chlorophenyl)-2,6-difluoropyrimidin-4-amine 4-Chloroaniline was added to a stirred solution of 2,4,6-trifluoropyrimidine (7.7 g), potassium carbonate (7.86 g) in ethanol (80 ml). The mixture was stirred at room temperature for 16 h, diluted with water, extracted with ethyl acetate, dried (MgSO4) and evaporated under reduced pressure. The residue was purified by chromatography on silica eluting with isohexane/ethyl acetate (4:1). Yield 8.3 g cream solid 1H NMR: (DMSO-d6) δ 10.47(1H, s), 7.58(211, d), 7.45(2H, d), 6.35(1H, s)

(ii) 4-[(4-Chlorophenyl)amino]-6-fluoropyrimidine-2-carbonitrile

Sodium cyanide (0.046 g) was added to a solution of the product from step (i) (0.113 g) in dimethylsulphoxide (3 ml) and stirred at room temperature for 1.5 h. The mixture was partitioned between ethyl acetate and water, the organics washed with water, dried (MgSO4), and evaporated under reduced pressure. The residue was purified by chromatography on silica eluting with isohexane/ethyl acetate (4:1). Yield 0.036 g 1H NMR: (DMSO-d6) δ 10.56(1H, s), 7.57(2H, d), 7.47(2H, d), 6.65(1H, s)

(iii) 4-[(4-Chlorophenyl)amino]-6-morpholin-4-ylpyrimidine-2-carbonitrile

Morpholine (0.16 g) was added to a solution of the product from step (ii) (0.16 g) in iso-propylalcohol (4 ml) and stirred for 2 h at room temperature. The mixture was partitioned between ethyl acetate and aqueous sodium hydrogencarbonate solution, the organics separated, dried (MgSO4) and evaporated under reduced pressure. The residue was purified by chromatography on silica eluting with isohexane/ethyl acetate (1:1). Yield 0.09 g MS: APCI(+ve) 316(M+1) 1H NMR: (DMSO-d6) δ 9.65 (1H, s), 7.52(2H, d), 7.38(2H, d), 6.08(1H, s), 3.67(4H, t), 3.48(2H, t)

EXAMPLES 28–42

Examples 28–42 were prepared according to the general method of example 27 using the appropriate amines or phenols

EXAMPLE 28

4-[(4-Methylcyclohexyl)amino]-6-morpholin-4-ylpyrimidine-2-carbonitrile

MS: APCI(+ve) 302(M+1) 1H NMR: (DMSO-d6) δ 7.21–7.18(1H, d), 5.83(H, s), 3.89(1H, bs), 3.88(4H, m), 3.41(4H, m), 1.63–1.28(9H, m), 0.89(3H, d)

EXAMPLE 29

4-(4-Chlorophenoxy)-6-morpholin-4-ylpyrimidine-2-carbonitrile

MS: APCI(–ve) 315(M–1) 1H NMR: (DMSO-d6) δ 7.53–7.20(4H, 2×d), 6.63(1H, s), 3.65–3.63(8H, m)

EXAMPLE 30

4-[(4-Chlorophenyl)amino]-6-(dimethylamino)pyrimidine-2-carbonitrile

MS: APCI(+ve) 274(M+1) 1H NMR: (DMSO-d6) δ 9.57 (1H, s), 7.55–7.34(4H, 2×d), 5.93(1H, s), 3.02(6H, m)

EXAMPLE 31

4[(1-Methylpiperidin 4-yl)amino]-morpholin-4-ylpyrimidine-2-carbonitrile, trifluoroacetate salt MS: APCI(+ve) 303(M+1) 1H NMR: (DMSO-d6) δ 9.36 (1H, brs), 7.49–7.47(1H, d), 5.76(1H, s), 3.92(1H, bm), 3.67–3.43(8H, 2×m), 3.34–3.10(4H, m), 2.75(3H, s), 2.07–1.68(4H, m)

EXAMPLE 32

4-(Cyclohexylamino)-6-morpholin-4-ylpyrimidine-2-carbonitrile

MS: APCI(+ve) 288(M+1) 1H NMR: (DMSO-d6) δ 7.23–7.21(1H, d), 5.73(1H, s), 3.62–3.42(9H, m), 1.83–1.07 (10H, m)

EXAMPLE 33

4[(4-Chlorophenyl)amino]-6-pyrrolidin-1-ylpyrimidine-2-carbonitrile

MS: APCI(+ve) 300(M+1) 1H NMR: (DMSO-d6) δ 9.55 (1H, s), 7.54–7.35(4H, 2×d), 5.79(1H, s), 3.38(4H, m), 1.93(4H, m)

EXAMPLE 34

4-[(6-Chloropyridin-3-yl)amino]-6-morpholin-4-ylpyrimidine-2-carbonitrile

MS: APCI(–ve) 315(M–1) 1H NMR: (DMSO-d6) δ 9.83 (1H, s), 8.55–8.49(1H, s), 8.06–8.02(1H, d), 7.49–7.46(1H, d), 6.10(1H, s), 3.69–3.66(4H, m), 3.52–3.48(4H, m)

EXAMPLE 35

1-{6-[(4-Chlorophenyl)amino]-2-cyanopyrimidin-4-yl}-L-prolinamide

MS: APCI(+ve) 343(M+1) 1H NMR: (DMSO-d6) δ 9.33 (1H, s), 7.57–7.24(4H, 2×d), 7.00(2H, bm), 5.81(1H, s), 4.31–3.38(3H, m), 2.26–1.26(4H, m)

EXAMPLE 36

4-(4-Aminopiperidin-1-yl)-6-[(4-chlorophenyl)amino]pyrimidine-2-carbonitrile, trifluoroacetate salt MS: APCI(+ve) 329(M+1) 1H NMR: (DMSO-d6) δ 9.66 (1H, s), 7.88–7.36(7H, m), 6.15(1H, s), 4.23–4.20(2H, m), 3.17–2.96(3H, m), 1.98–1.38(4H, m)

EXAMPLE 37

4-[(4-Chlorophenyl)amino]-6-(4-pyrrolidin-1-ylpiperidin-1-yl)pyrimidine-2-carbonitrile, acetate salt MS: APCI(+ve) 383(M+1) 1H NMR: (DMSO-d6) δ 9.57 (1H, s), 7.53–7.35(4H, 2×d), 6.09(1H, s), 4.06–2.51(9H, m), 1.92–1.90(5H, m), 1.74–1.34(6H, m)

EXAMPLE 38

4-[(4-Chlorophenyl)amino]-6-[(3-pyrrolidin-1-ylpropyl)amino]pyrimidine-2-carbonitrile, trifluoroacetate salt MS: APCI(+ve) 357(M+1) 1H NMR: (DMSO-d6) δ 9.52 (2H, m), 7.63–7.36(5H, 2×d+m), 5.92(1H, bs), 3.54–2.99 (8H, m), 2.00–1.84(6H, m)

EXAMPLE 39 tert-Butyl 4-{6-[(4-chlorophenyl)amino]-2-cyanopyrimidin-4-yl}piperazine-1-carboxylate MS: APCI(+ve) 415(M+1) 1H NMR: (DMSO-d6) δ 9.66 (1H, s), 7.52(2H—, d), 7.37(2H, d), 6.07(11H, s), 3.54–3.51 (4H, m), 3.44–3.41(4H, m), 1.42(9H, s)

EXAMPLE 40

4-[(4-Chlorophenyl)amino]-6-(cyclopropylamino)pyrimidine-2-carbonitrile

MS: APCI(+ve) 286(M+1) 1H NMR: (DMSO-d6) δ 9.65 (1H, s), 7.80(1H, s), 7.53(2H, d), 7.37(2H, d), 6.08(1H, s), 0.76–0.71(2H, m), 0.50–0.46(2H, m)

EXAMPLE 41

4-[(4-Chlorophenyl)amino]-6-piperazin-1-ylpyrimidine-2-carbonitrile

MS: APCI(+ve) 315(M+1) 1H NMR: (DMSO-d6) δ 9.62 (1H, s), 7.53(2H, d), 7.37(2H, d), 6.07(1H, s), 3.46(4H, t), 2.79(4H, t)

EXAMPLE 42

(2S)-N~2~-{6-[(4-Chlorophenyl)amino]-2-cyanopyrimidin-4-yl}-N~1~,N~1~-bis[4-(N-{6-[(4-chlorophenyl)amino]-2-cyanopyrimidin-4-yl}-L-leucyl)morpholin-3-yl]-L-leucinamide MS: APCI(+ve) 429(M+1) 1H NMR: (DMSO-d6) δ 9.51 (1H, s), 7.82(1H, d), 7.46(2H, d), 7.37(2H, d), 6.09(1H, s), 4.87(1H, s), 3.67–3.47(6H, m), 3.35–3.25(2H, m), 1.66–1.53(2H, m), 1.48–1.39(1H, m), 0.92–0.89(6H, m)

EXAMPLE 43

5-Chloro-4-[(4-chlorophenyl)amino]-6-morpholin-4-ylpyrimidine-2-carbonitrile (i) 4-(5-Chloro-2,6-difluoropyrimidin-4-yl)morpholine Morpholine (0.774 mg) was added to a solution of 5-chloro-2,4,6-trifluoropyrimidine (1.5 g), N,N-diisopropylethylamine (1.15 g) in 1,4-dioxane (30 ml) and stirred at room temperature for 16 h. The mixture was partitioned between ethyl acetate and water, the organic layer dried (MgSO4) and evaporated under reduced pressure. The residue was purified by chromatography on silica eluting with 8% ethyl acetate in isohexane. Yield 0.88 g (ii) 5-Chloro-N-(4-chlorophenyl)-2-fluoro-6-morpholin-4-ylpyrimidin-4-amine 4-Chloroaniline (1.44 g) was added to a solution of the product from step (i) (0.88 g) and N,N-diisopropylethylamine (0.484 g) in 1,4-dioxane (15 ml) and isopropylalcohol (15 ml) and the mixture heated at 110° C. for 6 days. The mixture was partitioned between ethyl acetate and water, the organics dried (MgSO4), and evaporated under reduced pressure. The solid was triturated with ethyl acetate, filtered and the filtrate purified by chromatography on silica eluting with 3% ethyl acetate in toluene. Yield 0.28 g MS: APCI(+ve) 343/5(M+1)

(iii) 5-Chloro-4-[(4-chlorophenyl)amino]-6-morpholin-4-ylpyrimidine-2-carbonitrile Sodium cyanide (0.057 g) was added to a solution of the product from step (ii) (0.2 g) in dimethylsulphoxide (5 ml) and the mixture stirred at room temperature. After 18 h, the mixture was partitioned between ethyl acetate and water, the organics separated, washed with water, dried (MgSO4) and evaporated under reduced pressure. The residue was purified by chromatography on silica eluting with 5% ethyl acetate in toluene. Yield 0.09 g MS: APCI(−ve) 348(M−1) 1H NMR: (DMSO-d6) δ 9.34 (1H, s), 7.53(2H, d), 7.42(2H, d), 3.71(4H, t), 3.55(4H, t)

EXAMPLE 44

4-[(4-Chlorophenyl)amino]-5-methoxy-6-piperazin-1-ylpyrimidine-2-carbonitrile, trifluoroacetate salt (i) 5-Methoxy-2-thioxodihydropyrimidine-4,6(1H,5H)-dione Thiourea (24 g) and methoxymethyl malonate (34 g) was added to a solution of sodium (12 g) in methanol and the mixture heated under reflux for 10 h. The methanol was evaporated under reduced pressure, water (500 ml) added and extracted with ether. The aqueous layer was acidified to pH1 with conc. hydrochloric acid, evaporated to ~200 ml and the precipitate filtered and dried. Yield 23 g 1H NMR: (DMSO-d6) δ 11.31(2H, s), 3.48(3H, s)

(ii) 2-(Ethylthio)-5-methoxypyrimidine-4,6(1H,5H)-dione

Ethyl iodide (11.2 ml) was added dropwise to a stirred mixture of the product from step (i) (23 g) and sodium hydroxide (6 g) in water (400 ml). After 16 h the mixture was filtered, the filtrate acidified to pH1 and the precipitate filtered, washed with water and dried. Yield 17.8 g 1H NMR: (DMSO-d6) δ 12.25(1H, s), 3.59(3H, s), 3.57 (1H, s), 3.06(2H, q), 1.28(3H, t)

(iii) 4,6-Dichloro-2-(ethylthio)-5-methoxypyrimidine

A mixture of the product from step (ii) (17.8 g) and N,N-diethylaniline (20 ml) in phosphorus oxychloride (400 ml) was heated at 100° C. for 3 h. The excess reagent was removed under reduced pressure and the residue poured onto ice and extracted with ether. The ether layer was washed with water, dried (MgSO4) and evaporated under reduced pressure. The residue was purified by chromatography on silica eluting with 5% ethyl acetate in isohexane. Yield 12.8 g (iv) 6-Chloro-N-(4-chlorophenyl)-2-(ethylthio)-5-methoxy-pyrimidin-4-amine A solution of the product from step (iii) (4 g) and 4-chloroaniline (5.3 g) in ethanol (40 ml) was heated under reflux for 16 h then the solvent removed under reduced pressure. The residue was partitioned between ethyl acetate and 2M hydrochloric acid, the organics washed with water, dried (MgSO4) and evaporated under reduced pressure. The residue was purified by chromatography on silica eluting with 10–15% ethyl acetate in isohexane. Yield 4.99 g MS: APCI(+ve) 330/2(M+1)

(v) 4-Chloro-6-[(4-chlorophenyl)amino]-5-methoxypyrimidine-2-carbonitrile

A mixture of the product from step (iv) (4.9 g) and 3-chloroperoxybenzoic acid (10 g, Aldrich 77% max.) in dichloromethane (150 ml) was stirred at room temperature for 3 h, washed with aqueous sodium metabisulphite solution, water, aqueous sodium hydrogencarbonate solution, water, dried (MgSO4) and evaporated under reduced pressure. The solid was dissolved in dimethylsulphoxide (40 ml), sodium cyanide (1.1 g) added and stirred for 2 h at room temperature. The mixture was partitioned between ethyl acetate and water, the organics dried (MgSO4) and evaporated under reduced pressure. The residue was purified by chromatography on silica eluting with 30% ethyl acetate in isohexane. Yield 3.23 g MS: APCI(+ve) 295/7(M+1)

(vi) 4-[(4-Chlorophenyl)amino]-5-methoxy-6-piperazin-1-ylpyrimidine-2-carbonitrile A solution of the product from step (v) (0.25 g) and piperazine (0.366 g) in tetrahydrofuran (8 ml) was heated at 60° C. for 6 h then the solvent removed under reduced pressure. The residue was purified by RPHPLC 15–75% acetonitrile in aqueous trifluoroacetic acid. Yield 0.139 g MS: APCI(+ve) 345(M+1) 1H NMR: (DMSO-d6) δ 9.29 (1H, s), 8.92(2H, s), 7.67(2H, d), 7.40(2H, d), 3.83–3.80(4H, m), 3.69(3H, s), 3.25–3.23(4H, m) Mpt 230° C.

EXAMPLES 45–51

Examples 45–51 were prepared according to the method of example 44 using the appropriate amines

EXAMPLE 45

4-[(4-Chlorophenyl)amino]-5-methoxy-6-morpholin-4-ylpyrimidine-2-carbonitrile MS: APCI(+ve) 346(M+1) 1H NMR: (DMSO-d6) δ 9.20 (1H, s), 7.67(2H, d), 7.38(2H, d), 3.73–3.70(4H, m), 3.68 (3H, s), 3.63–3.61(4H, m) Mpt 176° C.

EXAMPLE 46

4-[(3S)-3-Aminopyrrolidin-1-yl]-6-[(4-chlorophenyl)amino]-5-methoxypyrimidine-2-carbonitrile, trifluoroacetate salt MS: APCI(+ve) 345/7(M+1) 1H NMR: (DMSO-d6) δ 9.12(1H, s), 8.10(3H, s), 7.66(2H, d), 7.38(2H, d), 3.91–3.69 (5H, m), 3.65(3H, s), 2.33–2.22(1H, m), 2.08–2.01(1H, m) Mpt 345–7° C.

EXAMPLE 47

4-[(4-Chlorophenyl)amino]-6-{4-[3-(dimethylamino)propyl]piperazin-1-yl}-5-methoxypyrimidine-2-carbonitrile, bis-trifluoroacetate salt MS: APCI(+ve) 430/2(M+1) 1H NMR: (DMSO-d6) 90° C. δ 8.94(11, s), 7.64(2H, d), 7.35(2H, d), 3.81(4H, brs), 3.70(3H, s), 3.15–3.09(2H, m), 3.00(4H, brs), 2.86(2H, brs), 2.81(6H, s), 2.03–1.95(2H, m) Mpt 210–2° C.

EXAMPLE 48

4-[(4-Chlorophenyl)amino]-6-(dimethylamino)$_5$-methoxypyrimidine-2-carbonitrile MS: APCI(−ve) 302/4(M−1) 1H NMR: (DMSO-d6) 90° C. δ 9.08(1H, s), 7.66(2H, d), 7.37(2H, d), 3.62(3H, s), 3.13(6H, s) Mpt 173° C.

EXAMPLE 49

4-[(4-Chlorophenyl)amino]-5-methoxy-6(3-oxopiperazin-1-yl)pyrimidine-2-carbonitrile MS: APCI(−ve) 357/9(M−1) 1H NMR: (DMSO-d6) δ 9.24(1H, s), 8.10(1H, s), 7.67(2H, d), 7.39(2H, d), 4.17(2H, s), 3.85–3.83(2H, m), 3.66(3H, s), 3.32–3.29(2H, m) Mpt 244° C.

EXAMPLE 50

1-{6-[(4-Chlorophenyl)amino]-2-cyano-5-methoxypyrimidin-4-yl}piperidine-3-carboxamide MS: APCI(+ve) 387/9 (M+1) 1H NMR: (DMSO-d6) δ 9.16(1H, s), 7.68(2H, d), 7.40–7.35(3H, m), 6.89(1H, s), 4.34–4.25(2H, m), 3.65(3H, s), 3.07–2.92(2H, m), 2.35–2.40(1H, m), 1.90–1.51(4H, m)

EXAMPLE 51

4-(4-Aminopiperidin-1-yl)-6-[(4-chlorophenyl)amino]-5-methoxypyrimidine-2-carbonitrile, trifluoroacetate salt MS: APCI(+ve) 359/61 (M+1) 1H NMR: (DMSO-d6) δ 9.20(1H, s), 7.93(3H, s), 7.67(2H, d), 7.39(2H, d), 4.36–4.32 (2H, m), 3.66(3H, s), 3.08–3.01(2H, m), 2.00–1.97(2H, m), 1.57–1.54(2H, m)

EXAMPLE 52

5-Amino-4-[(4-chlorophenyl)amino]-6-morpholin-4-ylpyrimidine-2-carbonitrile (i) N-(4-Chlorophenyl)-6-morpholin-4-yl-5-nitro-2-(propylthio)pyrimidin-4-amine Morpholine (1.31 ml) was added dropwise to a stirred solution of 4,6-dichloro-5-nitro-2-thiopropyl pyrimidine (4 g), N,N-diisopropylamine (7 ml) in dichloromethane (50 ml) at 0° C. After 1 h, 4-chloroaniline (1.9 g) was added, the mixture stirred at room temperature for 24 h, then heated under reflux for 24 h. The mixture was partitioned between dichloromethane and 2M hydrochloric acid, the organics washed with water, dried (MgSO4) and evaporated under reduced pressure. Yield 5 g MS: APCI(+ve) 410/2 (M+1)

(ii) 4-[(4-Chlorophenyl)amino]-6-morpholin-4-yl-5-nitro-pyrimidine-2-carbonitrile A mixture of the product from step (i) (5 g) and 3-chloroperoxybenzoic acid (12 g, Aldrich 77% max.) in dichloromethane (200 ml) was stirred at room temperature for 2 h, washed with aqueous sodium metabisulphite solution, water, aqueous sodium hydrogencarbonate solution, water, dried (MgSO4) and evaporated under reduced pressure. The solid was dissolved in dimethylsulphoxide (30 ml), sodium cyanide (2 g) added and stirred for 1 h at room temperature. Water (500 ml) was added and the solid filtered, washed with water, dried and the residue triturated with ether. Yield 1.7 g MS: APCI(+ve) 361/3 (M+1)

(iii) 5-Amino-4-[(4-chlorophenyl)amino]-6-morpholin-4-ylpyrimidine-2-carbonitrile The product from step (ii) (1.7 g) and 10% palladium on charcoal (0.2 g) in ethyl acetate (300 ml) was hydrogenated at 2 Bar for 8 h, filtered through celite and the solvent evaporated under reduced pressure. Yield 1.05 g MS: APCI(+ve) 329/331 (M+1) 1H NMR: (DMSO-d6) δ 8.66(1H, s), 7.62(2H, d), 7.39(2H, d), 5.53(2H, s), 3.78–3.76 (4H, m), 3.08–3.06(4H, m) Mpt 253–4° C.

EXAMPLE 53

5-Amino-4[(4-Chlorophenyl)amino]-6(ethylamino) pyrimidine-2-carbonitrile

Example 53 was prepared according to the general method of example 52 using the appropriate amine MS: APCI(+ve) 289/91(M+1) 1H NMR: (DMSO-d6) δ 8.19(1H, s), 7.50(2H, d), 7.31(2H, d), 6.52(1H, t), 5.20(2H, s), 3.41–3.35(2H, m), 1.18(3H, t) Mpt 211–2° C.

Measurement of Cathepsin S Activity.

QFRET Technology (Quenched Fluorescent Resonance Energy Transfer) was used to measure the inhibition by test compounds of Cathepsin S-mediated cleavage of the synthetic peptide Z-Val-Val-Arg-AMC. Compounds were screened at five concentrations in duplicate and the pIC$_{50}$ values reported.

Synthetic substrate, 20 μM [final]Z-Val-Val-Arg-AMC in phosphate buffer were added to a 96 well black Optiplate. The assay plates were pre-read for compound auto fluorescence on SpectraMax Gemini at 355 nM excitation and 460 nM emission. 250 pM [final] rHuman Cathepsin S in phosphate buffer was added and incubated for 2 h at room temperature on the SpectraMax Gemini, taking readings every 20 min at 355 nM excitation and 460 nM emission.

Activity Based template (5PTB-8) used the auto fluorescent corrected data to calculate the percentage inhibition for each compound concentration using the relevent plate controls. This data was used to construct inhibition curves and $pIC_{50}$ estimated by non-linear regression using a 4 parameter logistic model.

What is claimed is:

1. A pharmaceutical composition which comprises a compound of formula (I):

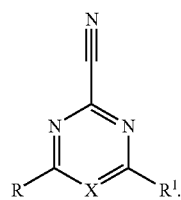

(I)

in which:
  X is CA where A is hydrogen, halogen, $CHR^2R^3$, $OR^2$, $NR^2R^3$, or $SR^2$;
  $R^2$ and $R^3$ are independently hydrogen, $C_{1-6}$ alkyl or $C_{3-6}$ cycloalkyl both of which can optionally contain one or more O, S or $NR^4$ groups where $R^4$ is hydrogen or $C_{1-6}$ alkyl, and can be optionally substituted by aryl, heteroaryl, $NR^5R^6$ where $R^5$ and $R^6$ together with the nitrogen atom to which they are attached form a 4–7 membered ring optionally containing a further O, S, $NR^4$, or R2 and R3 together with the nitrogen atom to which they are attached form a 4–7 membered ring optionally containing a further O, S, $NR^4$ group, or R2 and R3 are aryl or heteroaryl groups, both aryl and heteroaryl groups being optionally substituted by halogen, amino, hydroxy, cyano, nitro, carboxy, $CONR^7R^8$, $SO_2NR^7R^8$, $SO_2R^4$, trifluoromethyl, $NHSO_2R^4$, $NHCOR^4$, ethylenedioxy, methylenedioxy, $C_{1-6}$alkyl, $C_{1-6}$alkoxy, $NR^7R^8$ or $SR^7$ where $R^7$ and $R^8$ are independently hydrogen or $C_{1-6}$ alkyl;
  R and $R^1$ are independently a group $Y(CH_2)pR^9$ where p is 0, 1, 2 or 3 and Y is O or $NR^{10}$ where $R^{10}$ is hydrogen, $C_{1-6}$ alkyl or $C_{3-6}$ cycloalkyl; and $R^9$ is hydrogen, $C_{1-6}$ alkyl which can optionally contain one or more O, S or $NR^4$ groups where $R^4$ is hydrogen or $C_{1-6}$ alkyl, or a 3 to 7-membered saturated ring optionally containing a carbonyl group, one or more O, S or N atoms, or an aryl or heteroaryl group containing one to four heteroatoms selected from O, S or N, the saturated ring, aryl and heteroaryl groups all being optionally substituted by halogen, amino, hydroxy, cyano, nitro, carboxy, $CONR^7R^8$, $SO_2NR^7R^8$, $SO_2R^4$, trifluoromethyl, $NHSO_2R^4$, $NHCOR^4$, ethylenedioxy, methylenedioxy, $C_{1-6}$ alkyl, $C_{1-6}$alkoxy, $SR^5$ or $NR^{11}R^{12}$ where $R^{11}$ and $R^{12}$ are independently hydrogen, $C_{1-6}$ alkyl or together with the nitrogen atom to which they are attached form a 5- or 6-membered saturated ring optionally containing a further O, S or $NR^4$ group; or $R/R^1$ is a group $NR^{10}(CHR^{10})_q CONR^2R^3$ or $NR^{10}(CH_2)_q CONR^2R^3$ where q is 1, 2 or 3; or $R/R^1$ is a group $NR^{13}R^{14}$ where $R^{13}$ and $R^{14}$ together with the nitrogen atom to which they are attached form a 4 to 7-membered saturated ring optionally containing a carbonyl group, O, S or N atom and optionally substituted by $C_{1-6}$alkyl, amino, hydroxy, $CO_2C_{1-6}$alkyl, halogen, $NR^5R^6$, $NR^7R^8$, $C_{1-6}$alkyl$NR^{17}R^{18}$ where $R^{17}$ and $R^{18}$ are independently hydrogen or $C_{1-6}$ alkyl, $CONR^{15}R^{16}$ where $R^{15}$ and $R^{16}$ are independently hydrogen or $C_{1-6}$ alkyl, or optionally substituted by aryl, phenoxy, COphenyl, or a heteroaryl group, the latter four groups being optionally substituted by halogen, amino, hydroxy, cyano, nitro, carboxy, $CONR^7R^8$, $SO_2NR^7R^8$, $SO_2R^4$, trifluoromethyl, $NHSO_2R^4$, $NHCOR^4$, ethylenedioxy, methylenedioxy, $C_{1-6}$alkyl, $C_{1-6}$alkoxy, $SR^5$ or $NR^{11}R^{12}$ where $R^{11}$ and $R^{12}$ are independently hydrogen, $C_{1-6}$ alkyl or together with the nitrogen atom to which they are attached form a 5- or 6-membered saturated ring optionally containing a further O, S or $NR^4$ group; or a pharmaceutically acceptable salt thereof;

and a pharmaceutically acceptable diluent or carrier.

2. A method treating rheumatoid arthritis in a mammal comprising administering an effective amount of a compound of formula (I) to said mammal

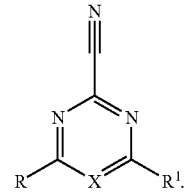

(I)

in which:
  X is CA where A is hydrogen, halogen, $CHR^2R^3$, $OR^2$, $NR^2R^3$, or $SR^2$;
  $R^2$ and $R^3$ are independently hydrogen, $C_{1-6}$alkyl or $C_{3-6}$ cycloalkyl both of which can optionally contain one or more O, S or $NR^4$ groups where $R^4$ is hydrogen or $C_{1-6}$alkyl, and can be optionally substituted by aryl, heteroaryl, $NR^5R^6$ where $R^5$ and $R^6$ together with the nitrogen atom to which they are attached form a 4–7 membered ring optionally containing a further O, S, $NR^4$, or R2 and R3 together with the nitrogen atom to which they are attached form a 4–7 membered ring optionally containing a further O, S, $NR^4$ group, or R2 and R3 are aryl or heteroaryl groups, both aryl and heteroaryl groups being optionally substituted by halogen, amino, hydroxy, cyano, nitro, carboxy, $CONR^7R^8$, $SO_2NR^7R^8$, $SO_2R^4$, trifluoromethyl, $NHSO_2R^4$, $NHCOR^4$, ethylenedioxy, methylenedioxy, $C_{1-6}$alkyl, $C_{1-6}$alkoxy, $NR^7R^8$ or $SR^7$ where $R^7$ and $R^8$ are independently hydrogen or $C_{1-6}$alkyl;
  R and $R^1$ are independently a group $Y(CH_2)pR^9$ where p is 0, 1, 2 or 3 and Y is O or $NR^{10}$ where $R^{10}$ is hydrogen, $C_{1-6}$alkyl or $C_{3-6}$cycloalkyl;
and $R^9$ is hydrogen, $C_{1-6}$alkyl which can optionally contain one or more O, S or $NR^4$ groups where $R^4$ is hydrogen or $C_{1-6}$ alkyl, or a 3 to 7-membered saturated ring optionally containing a carbonyl group, one or more O, S or N atoms, or an aryl or heteroaryl group containing one to four heteroatoms selected from O, S or N, the saturated ring, aryl and heteroaryl groups all being optionally substituted by halogen, amino, hydroxy, cyano, nitro, carboxy, $CONR^7R^8$, $SO_2NR^7R^8$, $SO_2R^4$, trifluoromethyl, $NHSO_2R^4$, $NHCOR^4$, ethylenedioxy, methylenedioxy, $C_{1-6}$alkyl, $C_{1-6}$alkoxy, $SR^5$ or $NR^{11}R^{12}$ where $R^{11}$ and $R^{12}$ are independently hydrogen, $C_{1-6}$alkyl or together with the nitrogen atom to which they are attached form a 5- or 6-membered saturated ring optionally containing a further O, S or NR$^4$ group; or R/R$^1$ is a group NR$^{10}$(CHR$^{10}$) CONR$^2$R$^3$ or NR$^{10}$(CH$_2$)$_q$CONR$^2$R$^3$ where q is 1, 2 or 3; or R/R$^1$ is a group NR$^{13}$R$^{14}$ where R$^{13}$ and R$^{14}$ together with the nitrogen atom to which they are attached form a 4 to 7-membered saturated ring optionally containing a carbonyl group, O, S or N atom and optionally substituted by C$_{1-6}$ alkyl, amino, hydroxy, CO$_2$C$_{1-6}$alkyl, halogen, NR$^5$R$^6$, NR$^7$R$^8$, C$_{1-6}$ alkylNR$^{17}$R$^{18}$ where R$^{17}$ and R$^{18}$ are independently hydrogen or C$_{1-6}$ alkyl, CONR$^{15}$R$^{16}$ where R$^{15}$ and R$^{16}$ are independently hydrogen or C$_{1-6}$ alkyl, or optionally substituted by aryl, phenoxy, COphenyl, or a heteroaryl group, the latter four groups being optionally substituted by halogen, amino, hydroxy, cyano, nitro, carboxy, CONR$^7$R$^8$, SO$_2$NR$^7$R$^8$, SO$_2$R$^4$, trifluoromethyl, NHSO$_2$R$^4$, NHCOR$^4$, ethylenedioxy, methylenedioxy, C$_{1-6}$alkyl, C$_{1-6}$alkoxy, SR$^5$ or NR$^{11}$R$^{12}$ where R$^{11}$ and R$^{12}$ are independently hydrogen, C$_{1-6}$alkyl or together with the nitrogen atom to which they are attached form a 5- or 6-membered saturated ring optionally containing a further O, S or NR$^4$ group;

or a pharmaceutically acceptable salt.

3. The method according to claim 2 in which A is H, NHR$^2$, or OR$^2$ wherein R$^2$ is hydrogen or C$_{1-6}$alkyl.

4. The method according to claim 2 in which R is a group Y(CH$_2$)pR$^7$ where p is 0 or 1 and Y is NR$^8$ wherein R$^8$ is hydrogen and R$^7$ is substituted phenyl.

5. The method according to claim 2 in which R$^1$ is a group NR$^{13}$R$^{14}$ where R$^{13}$ and R$^{14}$ together with the nitrogen atom to which they are attached form a morpholine ring, piperidine or piperazine ring optionally substituted.

6. The method according to claim 2 in which R$^1$ is a group NR$^9$R$^{10}$ where R$^{10}$ is H or C$_{1-6}$alkyl and R$^9$ is C$_{1-6}$alkyl which can optionally contain one or more O, S or NR$^4$ groups where R$^4$ is hydrogen or C$_{1-6}$alkyl.

7. The method according to claim 2 where the compound of formula (I) is selected from:
  4-[(4-Chlorophenyl)amino]-6-morpholin-4-ylpyrimidine-2-carbonitrile,
  4-[(4-Methylcyclohexyl)amino]-6-morpholin-4-ylpyrimidine-2-carbonitrile,
  4-(4-Chlorophenoxy)-6-morpholin-4-ylpyrimidine-2-carbonitrile,
  4-[(4-Chlorophenyl)amino]-6-(dimethylamino)pyrimidine-2-carbonitrile,
  4-[(1 -Methylpiperidin-4-yl)amino]-6-morpholin-4-ylpyrimidine-2-carbonitrile,
  4-(Cyclohexylamino)-6-morpholin-4-ylpyrimidine-2-carbonitrile,
  4-[(4-Chlorophenyl)amino]-6-pyrrolidin-1-ylpyrimidine-2-carbonitrile,
  4-[(6-Chloropyridin-3-yl)amino]-6-morpholin-4-ylpyrimidine-2-carbonitrile,
  1 -{6-[(4-Chlorophenyl)amino]-2-cyanopyrimidin-4-yl}-L-prolinamide,
  4-(4-Aminopiperidin- 1-yl)-6-[(4-chlorophenyl)amino]pyrimidine-2-carbonitrile,
  4-[(4-Chlorophenyl)amino]-6-(4-pyrrolidin-1-ylpiperidin-1-yl)pyrimidine-2-carbonitrile,
  4-[(4-Chlorophenyl)amino]-6-[(3-pyrrolidin-1 -ylpropyl)amino]pyrimidine-2-carbonitrile,
  tert-Butyl 4-{6-[(4-chlorophenyl)amino]-2-cyanopyrimidin-4-yl}piperazine-1-carboxylate,
  4-[(4-Chlorophenyl)amino]-6-(cyclopropylamino)pyrimidine-2-carbonitrile,
  4-[(4-Chlorophenyl)amino]-6-piperazin-1-ylpyrimidine-2-carbonitrile,
  (2S)-N~2~-{6-[(4-Chlorophenyl)amino]-2-cyanopyrimidin-4-yl}-N~1~,N~1~-bis [4-(N-{6-[(4-chlorophenyl)amino]-2-cyanopyrimidin-4-yl}-L-leucyl)morpholin-3-yl]-L-leucinamide,
  5-Chloro-4-[(4-chlorophenyl)amino]-6-morpholin-4-ylpyrimidine-2-carbonitrile,
  4-[(4-Chlorophenyl)amino]-5-methoxy-6-piperazin-1-ylpyrimidine-2-carbonitrile,
  4-[(4-Chlorophenyl)amino]-5-methoxy-6-morpholin-4-ylpyrimidine-2-carbonitrile,
  4-[(3S)-3-Aminopyrrolidin-1-yl]-6-[(4-chlorophenyl)amino]-5-methoxypyrimidine-2-carbonitrile,
  4-[(4-Chlorophenyl)amino]-6-{4-[3-(dimethylamino)propyl]piperazin-1 -yl}-5-methoxypyrimidine-2-carbonitrile,
  4-[(4-Chlorophenyl)amino]-6-(dimethylamino)-5-methoxypyrimidine-2-carbonitrile,
  4-[(4-Chlorophenyl)amino]-5-methoxy-6-(3-oxopiperazin-1 -yl)pyrimidine-2-carbonitrile,
  1-{6-[(4-Chlorophenyl)amino]-2-cyano-5-methoxypyrimidin-4-yl}piperidine-3-carboxamide,
  4-(4-Aminopiperidin-1-yl)-6-[(4-chlorophenyl)amino]-5-methoxypyrimidine-2-carbonitrile,
  5-Amino-4-[(4-chlorophenyl)amino]-6-morpholin-4-ylpyrimidine-2-carbonitrile, and
  5-Amino-4-[(4-Chlorophenyl)amino]-6-(ethylamino)pyrimidine-2-carbonitrile.

* * * * *